United States Patent
Ory et al.

(10) Patent No.: US 6,391,060 B1
(45) Date of Patent: May 21, 2002

(54) PROSTHETIC IMPLANT FOR OBSTRUCTING AN ANATOMICAL DUCT, AND OBSTRUCTING ASSEMBLY COMPRISING SAME

(75) Inventors: François Régis Ory, Fontaines Saint Martin; Michel Therin, Lyons, both of (FR)

(73) Assignee: Sofradim Productions, Trevoux (FR)

( * ) Notice: Subject to any disclaimer, the term of this patent is extended or adjusted under 35 U.S.C. 154(b) by 0 days.

(21) Appl. No.: 09/529,353

(22) PCT Filed: Oct. 21, 1998

(86) PCT No.: PCT/IB98/01675

§ 371 Date: Apr. 13, 2000

§ 102(e) Date: Apr. 13, 2000

(87) PCT Pub. No.: WO99/20204

PCT Pub. Date: Apr. 29, 1999

(30) Foreign Application Priority Data

Oct. 22, 1997 (FR) ............................................. 97 13464

(51) Int. Cl.[7] ................................................. A61F 2/02
(52) U.S. Cl. .................................... 623/23.76; 606/151
(58) Field of Search .......................... 623/11.11, 23.72, 623/23.74, 23.76; 606/151, 153, 155, 156, 213, 214, 215, 37

(56) References Cited

U.S. PATENT DOCUMENTS 5,397,331 A * 3/1995 Himpens ................. 623/11.11
5,575,759 A * 11/1996 Moll ....................... 623/11.11
5,716,409 A * 2/1998 Debbas ................... 623/11.11
5,824,082 A * 10/1998 Brown .................... 623/11.11
5,922,026 A * 7/1999 Chin ....................... 623/11.11
6,066,776 A * 5/2000 Goodwin ................ 623/11.11
6,224,616 B1 * 5/2001 Kugel ..................... 623/11.11
6,241,768 B1 * 6/2001 Agarwal ................. 623/11.11

FOREIGN PATENT DOCUMENTS

| EP | 0 544 485 A1 | 6/1993 |
| EP | 0 614 650 A2 | 9/1994 |
| JP | 5-237128 A * | 9/1993 |
| WO | WO 92/06639 | 4/1992 |
| WO | WO 94/17747 | 8/1994 |
| WO | WO 95/32687 | 12/1995 |

* cited by examiner

Primary Examiner—David H. Willse
(74) Attorney, Agent, or Firm—Oliff & Berridge, PLC

(57) ABSTRACT

A prosthetic implant for obturating an anatomical duct, cavity or orifice, has a porous textile element obtained from a prosthetic fabric, having a flat and nongathered up configuration in the shape of a patch with a continuous outer edge or periphery. The implant has at least two radial elements extending and distributed around a central zone free from any radial element. The radial element centripetally stresses the remaining periphery of the textile element. A peripheral zone having radial elements is comprised of at least two superimposed panels of prosthetic fabric. The radial elements are in the shape of textile strips and consist of a multiplicity of stitches linking the two panels with at least one thread.

12 Claims, 5 Drawing Sheets

PROSTHETIC IMPLANT FOR OBSTRUCTING AN ANATOMICAL DUCT, AND OBSTRUCTING ASSEMBLY COMPRISING SAME

The present invention relates to a prosthetic implant for obturating an anatomical duct, cavity or orifice and will be more particularly described by way of example for use in the treatment of hernias of the groin.

Various prosthetic implants for obturating hernial orifices are known in the prior art in the form of textile elements, strips or rectangles, wound in order to form either a cylinder or a cone. Such elements are then inserted in the orifice to be obturated. A certain number of technical solutions have been described, in particular in the documents U.S. Pat. No. 5,356,432, U.S. Pat. No. 5,116,357, U.S. Pat. No. 5,147,374 and U.S. Pat. No. 5,456,720. They all have in common the preforming, for example by thermoforming, of these cones or cylinders.

For example, according to FIG. 17 of the document EP-A-0544485, a prosthetic implant for obturating an anatomical duct, cavity or orifice is described as comprising a one-piece porous textile element obtained from a prosthetic fabric.

In a flat and nongathered-up configuration, this porous element has the shape of a textile patch with a continuous outer edge or periphery. It comprises several reinforcing radial elements, interlaced in the textile patch, extending and distributed around a central zone free from any said element. These reinforcing elements determine, by local thrust in said central zone, whilst centripetally stressing the remaining periphery of the textile element, a configuration gathered up in volume.

However, these prior solutions have several problems related to this preforming, particularly because the prosthetic implants which result from it are often too rigid. This results in the following disadvantages:

the obturating prosthetic implant is traumatizing or perforating with regard to the peritoneal structures and can adapt only with difficulty to the thickness of the abdominal wall;

the cone or cylinder shapes of the prosthetic implant do not favor its congruence with the complex geometry of a hernial orifice;

obturating prosthetic implants are subject to a lot of contact with the surgeon's hands, thus increasing the risk of post operative infection;

traditional preformed obturating prosthetic implants do not allow the surgeon to reach sites not accessible with a finger.

The subject of the present invention is a prosthetic implant, as described above, having practically no privileged or residual shape, and therefore retaining good conformability, whilst nevertheless offering a certain rigidity during its manipulation, on the one hand in order to be inserted in gathered-up form into the anatomical orifice to be obturated and, on the other hand, to press in this form against the edge or the wall of said orifice, all of this in a nontraumatizing or hardly traumatizing manner.

A prosthetic implant according to the present invention combines the following characteristics:

it is in the textile element that are included and located without break, both the central zone free of any radial element and the peripheral zone which comprises these radial elements; the central zone is therefore filled by the textile element itself, and is not therefore occupied by another element or piece, in particular an added one.

the textile element will comprise at least two panels of superimposed prosthetic fabric;

and the two radial elements are shaped like two textile strips respectively, each consisting of a multiplicity of stitches linking, particularly by sewing or knitting, said two panels, with at least one thread.

Preferably, but not exclusively, in the gathered-up configuration, the two radial elements determine at least two opposite hollow, open or closed lobes formed by the two panels between said radial elements. This lobed configuration favors consistency of the textile element in its gathered-up configuration.

The present invention also relates to an obturating assembly comprising a prosthetic implant such as described above, and an applicator.

In effect, it has been found that a prosthetic implant according to the invention would exhibit the advantage that not preforming the implant in the shape of a cylinder or cone would favor its congruence with the complex geometry of an anatomical orifice, duct or cavity, for example hernial.

Preferably, the radial elements each extend radially from the outer edge of the textile element to an intermediate point between a geometric center of said textile element and the outer edge of said textile element.

More preferably, the radial elements each extend radially up to the central zone.

In preferred embodiment, the radial elements each extend radially over a limited length, starting from and in the vicinity of the outer edge.

Preferably, the two panels are connected to each other by discontinuous overstitching along the outer edges of the panels, in such a way as to determine open lobes in the gathered-up configuration of the implant.

According to a preferred embodiment, the two panels are connected to each other by the radial elements tying the two panels.

In another preferred embodiment, the textile element comprises at least three panels bound to each other, of identical or different nature, one of the panels possibly having a three-dimensional structure.

In a preferred way, the textile element is capable of being obtained by cutting out a circular patch bringing together an outer panel, an intermediate panel and an inner panel, by folding said patch along a diameter with two sides facing each other, radial elements connecting the three panels together, and at least two elements connecting the two sides facing each other of the inner panel.

Still more preferably, the radial elements connect two panels to each other, the third panel being connected to the other two by overstitching its outer edge.

In a preferred embodiment, the implant, the implant comprises an additional covering panel, bound to the textile element, having a shape different from that of the latter and adapted with an appropriate slit for surrounding any anatomical duct.

The present invention will be understood better from the detailed description of preferred embodiments given by way of example only, and referring to the appended drawing wherein.

Figure 1:
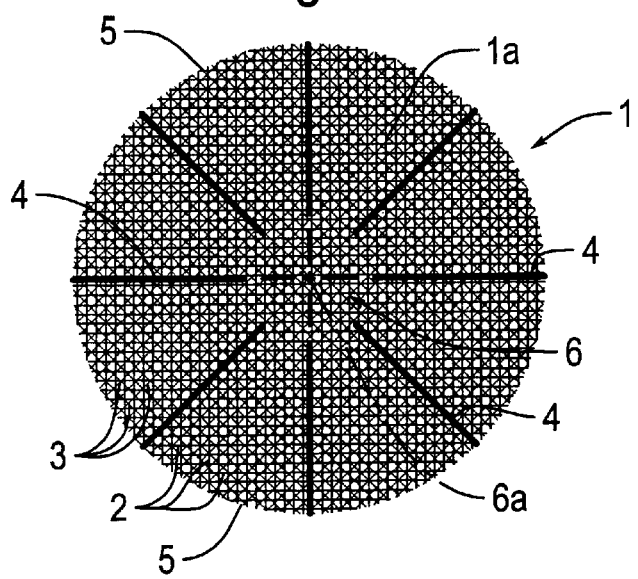
FIG. 1 is a plan view of an obturating prosthetic implant according to the invention, in its flat and nongathered-up configuration.

FIG. 1 shows an obturating prosthetic implant 1 according to the present invention, seen in plan view from above. The prosthetic implant is of generally circular shape, and has, for example, a diameter of about 8 cm. This shape can of course be varied, and it is possible to use, for example, prosthetic implants of elliptical shape, having for example a diameter of between about 6.5 cm (minor diameter) and 8.5 cm (major diameter).

The obturating prosthetic implant 1, in its flat and nongathered-up configuration, comprises a porous textile element 1a, having the shape of a patch with a continuous outer edge or periphery 5, and is constituted by a panel 2 (upper according to FIG. 1) and a second panel 3 (lower according to FIG. 1), superimposed and each consisting of knitted warp and weft threads, of relatively flexible prosthetic fabric, for example made of biocompatible and non-resorbable polymer, and preferably based on multi-strand 50 dtex polyester threads. Such a prosthetic fabric is manufactured and marketed by the applicant under the reference PAC, and consists in a knitting with weft and warp threads, with square openings, produced with three Layers of warp threads. The fabric exhibits good bi-directional stability and does not fray on cutting. The two panels can of course be of the same or different nature, but generally each exhibit a squared two-dimensional structure, for example with pores of about 1.5 mm×1.5 mm. As can be seen in FIG. 1, in comparison with the squaring of the two-dimensional structure, the two panels can be offset angularly with respect to one another, and the panel 3 is preferably oriented at 45° with respect to the panel 2.

These two panels 2, 3 are connected to each other by radial plication guide elements 4 extending and distributed around a central zone 6 free of any said radial element. As will be better illustrated with reference to FIG. 13, the radial elements 4 determine, when a local thrust is applied, for example with a finger, in the central zone 6, whilst centripetally stressing the remaining periphery of the textile element 1a, a configuration gathered up in volume comprising at least two opposite hollow lobes 32, formed by the two panels 2 and 3 between the radial elements 4.

Preferably, these radial elements 4 are integrated in the textile element, tying the two panels and binding them to one another. Each radial element is shaped like a textile strip, consisting of a multiplicity of sewing stitches linking the panels 2 and 3 with at least one thread, preferably the same as the one used for knitting said prosthetic fabric. As shown in FIGS. 1 to 5, eight radial sewings 4, equally angularly distributed, start from the outer edge 5 of the panels, or from its vicinity, and go toward the central zone 6 and the geometric center 6a of the circle, for example over about 3 cm. If the panels are of elliptical shape, the radial sewings 4 are of unequal length and they converge toward the geometric center 6a of the ellipse, stopping for example about 1 cm from the latter. In this way the radial elements 4 do not extend right up to the geometric center 6a of the textile element 1a, but up to the central zone 6, which avoids the risk of a perforation or traumatism of sensitive organs in or around the orifice or duct to be obturated when the implant is in its gathered-up configuration.

Figure 2:
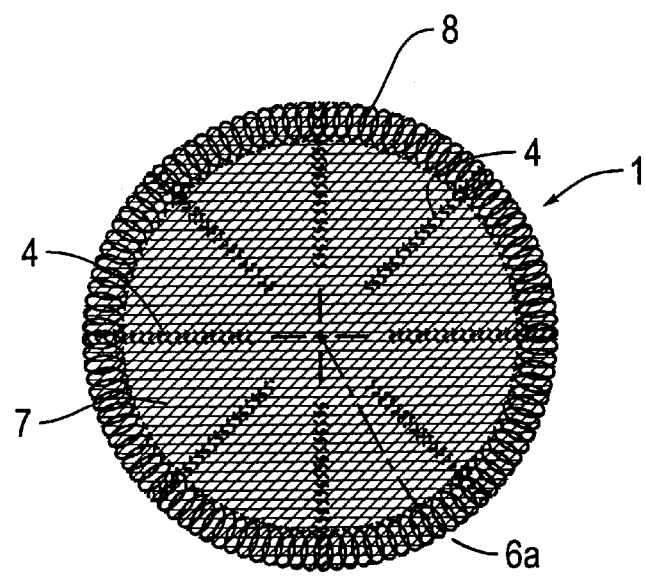
FIG. 2 shows a variant of the prosthetic implant of FIG. 1, seen from below with a textile element having three panels, in its flat and nongathered-up configuration.

As shown well in FIGS. 1 and 2, it is in the textile element 1a that are located and included without break both the central zone 6 free of any radial element 4, and the adjacent and peripheral zone comprising precisely these radial elements 4; such that an implant according to the present invention amounts to said textile element 1a with its radial elements 4, generally integrated.

The obturating prosthetic implant according to FIG. 2 is distinguished from the one shown according to FIG. 1 in that the textile element 1a furthermore comprises a third panel 7, preferably of porous three-dimensional structure suitable for rehabilitation, and having, for example, a thickness of about 1.5 to 2 mm. Such a panel is marketed by the applicant, under the name PAT. This panel is a three-dimensional warp knitting with ties, having two faces with hexagonal openings bound by a tie of warp threads, and which provides it with three-directional elasticity. The third panel is the one which will rest on the various organs during the repair of a direct inguinal hernia for example, and will protect that latter from possibly traumatizing contact with the panels 2 and 3.

The panels 2 and 3 are integrated with the third panel 7 by discontinuous overstitching 8 around the common circular edge 5 of said panels. The overstitching thread is preferably identical to that used for the radial elements 4.

The assembly obtained according to FIG. 2 can be optionally coated with collagen for example bovine type 1.

Figure 3:
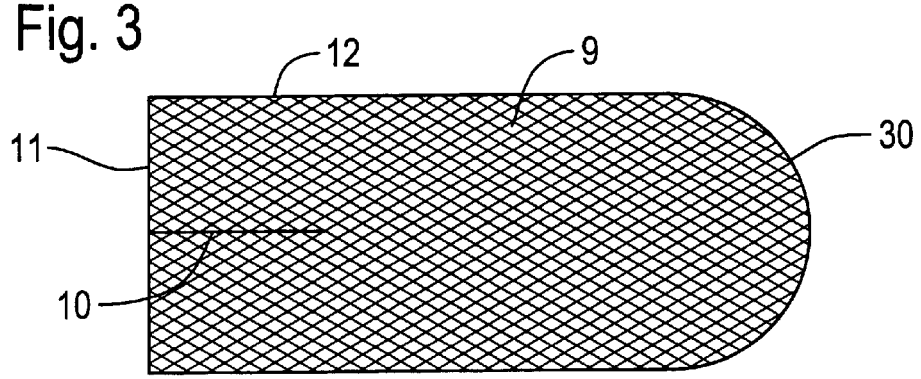
FIG. 3 shows an additional covering panel for the prosthetic implant of FIGS. 1 and 2.

FIG. 3 shows an additional covering panel for the prosthetic implant according to the invention. This panel 9 can have a width of about 4.5 cm and a length of about 11 cm, and is generally of rectangular shape. It comprises a slit 10, adapted to receive an anatomical duct, for example spermatic vessels in the case of hernial repair, and extending from a straight inner edge 11, or short side of the panel 9, preferably perpendicular to the transverse edge 12, or long side of the panel 9; the slit 10 extends to the middle of the panel, over a length of about 3 cm. Opposite the rounded outer edge 11 of the additional covering panel 9, the latter comprises another outer edge 30.

Figure 4:
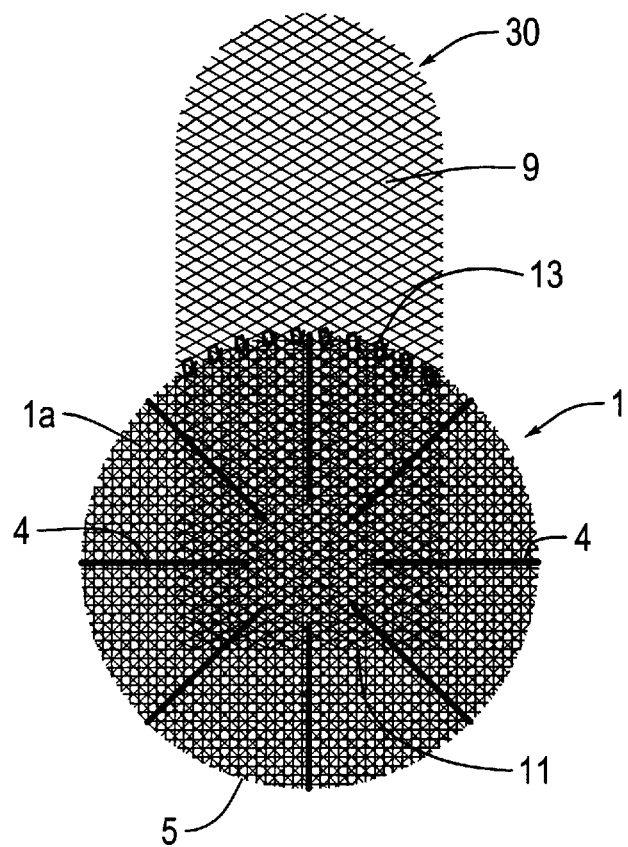
FIG. 4 shows a plan view, in its flat and nongathered-up configuration, of another preferred embodiment of the prosthetic implant according to the invention as shown in FIGS. 1 and 2, provided with the additional panel of FIG. 3.
Figure 5:
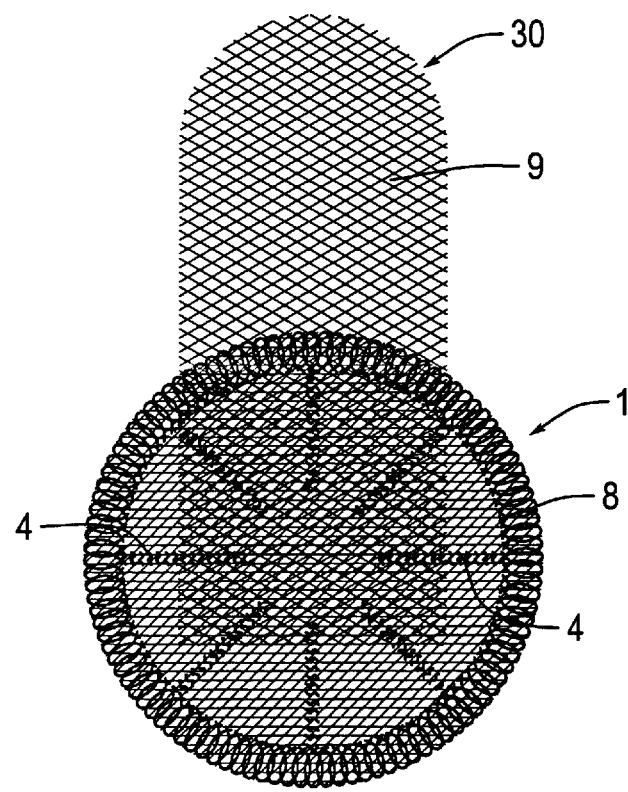
FIG. 5 shows a bottom view of the prosthetic implant according to FIG. 4.
Figure 6:
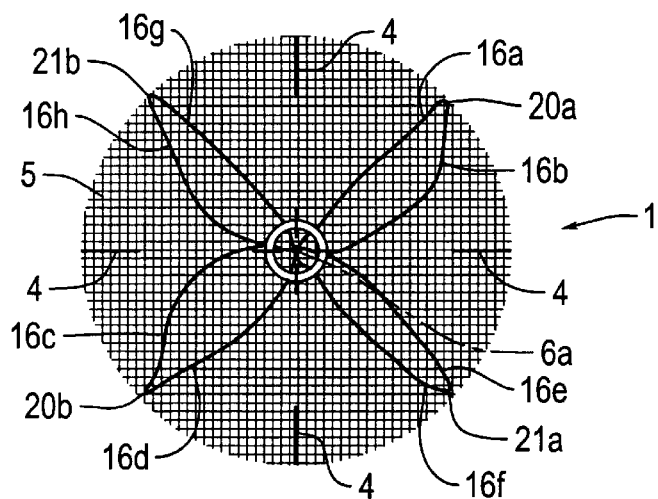
FIG. 6 shows a plan view of another preferred embodiment of the prosthetic implant according to the invention, in its flat and nongathered-up configuration, in an ancillary obturating assembly.
Figure 7:
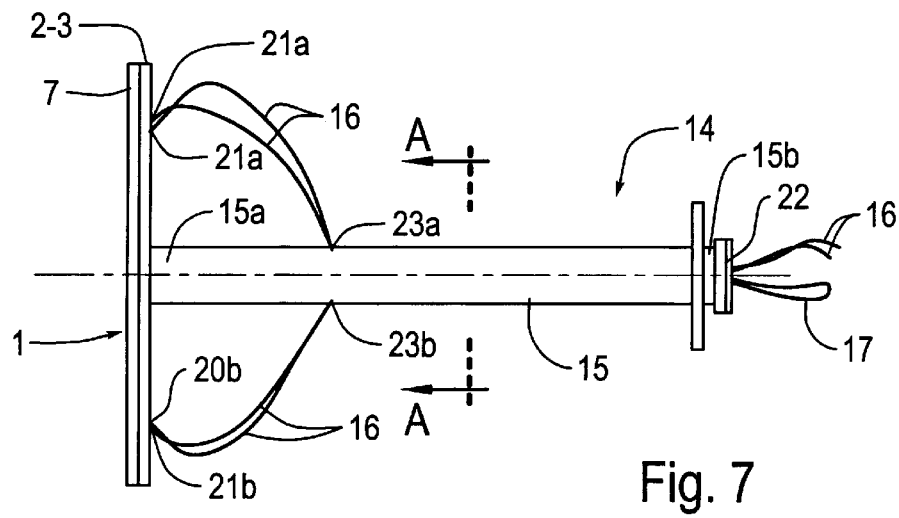
FIG. 7 shows a side view of the assembly according to FIG. 6.

As illustrated in FIGS. 4 and 5, which show top and bottom plan views respectively of the prosthetic implant according to the invention, the additional covering panel 9 is fixed to the textile element 1a, for example by sutures 13, such that the longitudinal axis of symmetry of said panel coincides with a diameter of the circular textile element 1a, with the inner edge 11 contained within the circle defined by said textile element, and the outer edge 30 outside of said circle. The fixing is advantageously carried out along the circular edge of the textile element 1a. The function of this additional covering panel is to protect the potentially fragile peripheral zones of the hernial orifice from risks of recurrence.

As said previously, the invention also relates to an obturating assembly comprising an obturating prosthetic implant 1 such as described previously and an applicator 14. This part of the invention is illustrated by FIGS. 6 to 9, wherein the only difference with respect to the prosthetic implant of the preceding figures is that the radial and plication guide elements 4, consist of only four sewings distributed radially about the geometric center 6a of the obturating implant and extending over a shorter distance toward the central zone 6. In the case of the present invention, an applicator 14 can consist of a rigid tubular element 15, for example a rigid channel, in which is passed a pulling thread 16, the thread 16 being freely interlaced in the panel 2 of the textile element 1, such that the ends of the thread 16, as well as a loop 17 formed from the thread 16 protrude from the open proximal end 15b of the tubular element 15. The thread 16 emerges from the tubular element 15 through openings 23a, 23b at a distance from the open distal end 15a of the tubular element 15, this distance corresponding for example at least to the distance separating the geometric center 6a of the textile element 1a from its outer edge 5, for example to at least 4 cm (radius of the circle of the obturating prosthetic implant). The thread 16 passes through an opening 23a toward the outer edge 5 according to reference 16a, and around a warp or weft thread at a place 20a on the panel 2, in order then to return according to reference 16b toward a place diametrically opposite 20b to the one previously described, either by passing again through the openings 23a and 23b, or directly according to reference 16c in order to return then toward the openings 23a, 23b according to reference 16d. This operation is begun again with the same thread 16 according to references 16e, 16f, 16g and 16h, at the places 21a, 21b, in order to form a crossed pattern; see FIG. 6.

In order to fold the prosthetic implant 1 before its insertion into the inguinal orifice, it then suffices to pull the loop 17 and the ends of the thread 16 at the open proximal end 15b of the tubular element 15. Given that the center of the open end 15b of the element 15 is connected with the geometric center 6a of the prosthetic implant 1, the latter will fold into a regular four-lobed shape 32 corresponding to the view shown in FIG. 8, which is a view along the line A—A of FIG. 7. It will be observed that the prosthetic implant 1 folds along the interlacing of the thread, but that this plication is also guided by the reinforcing and guide elements 4.

Figure 9:
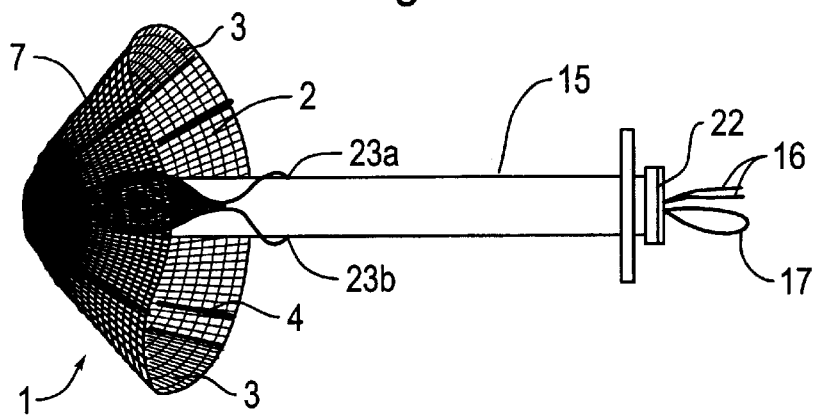
FIG. 9 shows a side perspective view of FIG. 8, after complete plication of the prosthetic implant in its gathered-up configuration.

By continuing the pulling on the thread 16 and the loop 17, the final configuration shown in FIG. 9 is reached, that is to say that the obturating prosthetic implant 1 is shaped like a rosette, ready for insertion by the surgeon into the anatomical duct, orifice or cavity. The applicator therefore makes it possible, with a single thread, for example looped, to gather up the obturating prosthetic implant 1 around the axis of the tubular element 15 simply by pulling. The withdrawal of the thread 16 is carried out by pulling on the loop 17 and thus releasing the implant in its site. The use of this applicator reduces contact between the surgeon's fingers and the body, and with the implant, and makes it possible to reach sites that are not accessible to a finger by itself.

Figure 8:
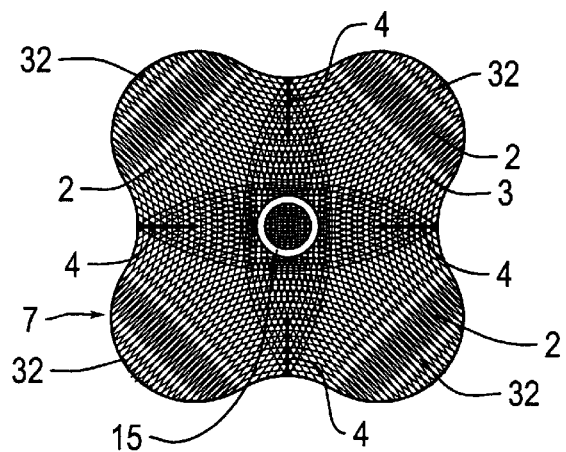
FIG. 8 shows a plan view of the prosthetic implant of FIG. 7 along the line A—A, after a beginning of plication of the latter toward its gathered-up configuration.

In the configuration of the obturating prosthetic implant 1 gathered up into a rosette, partial as shown in FIG. 8 and total in FIG. 9, each hollow lobe 32 is delimited between a quarter-of-a-circle section of the first panel 2, of external convex shape, and an opposite quarter of a circle section of the second panel 3, of internal concave shape, these sections being joined together by two radial elements 4, each common to two adjacent lobes 32. The four lobes 32 between them determine an internal cross shape.

Figure 10:
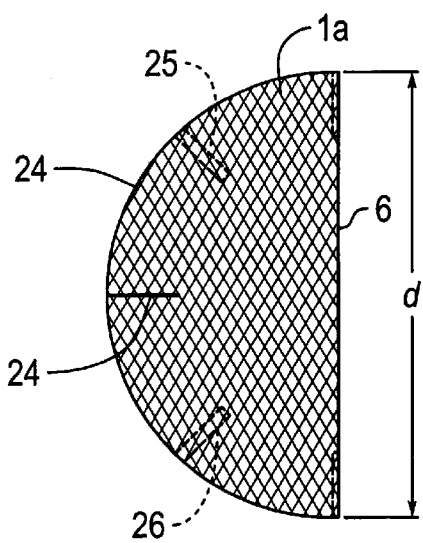
FIG. 10 shows a plan view of a prosthetic implant according to another embodiment according to the invention.
Figure 11:
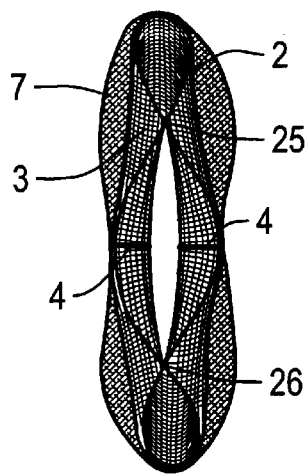
FIG. 11 shows a side view of the prosthetic implant of FIG. 10.
Figure 12:
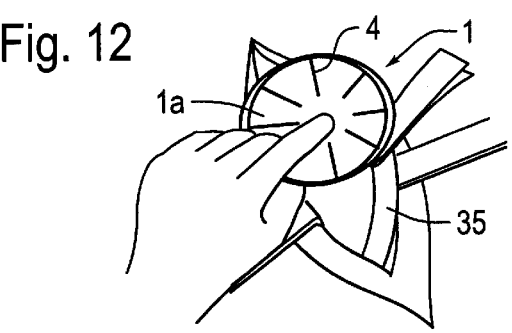
FIG. 12 is a diagrammatic view of the manipulation of an obturating implant according to FIGS. 1 and 2 in order to obturate an inguinal duct.

FIGS. 10 and 11 show another preferred embodiment of the obturating prosthetic implant according to the invention. This other embodiment will be described only with respect to the differences from the embodiments of FIGS. 1 to 5. The obturating implant 24 has a semicircular shape, in its flat nongathered-up form, and the textile element 1a is obtained by cutting out a circular patch bringing together three panels, inner 2, intermediate 3 and outer 7 respectively. This patch is folded into two facing sides along a diameter d of the textile element 1a, in such as way as to form a semicircle. The three panels are connected by radial elements 4, and the intermediate 3 and outer 7 panels are connected to one another by overstitching. The inner panel 2 however has at least two elements, for example sewings 25, 26 connecting its two facing sides (cf. FIG. 11).

Figure 13:
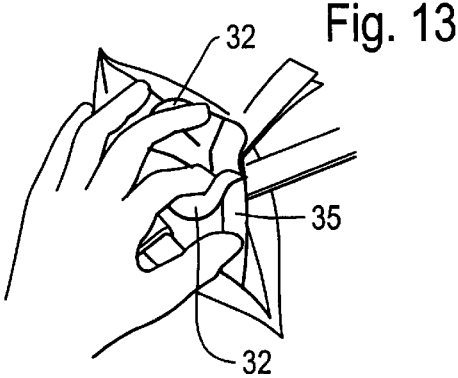
FIG. 13 is a diagrammatic view of the folding of the implant according to FIGS. 1 and 2 and its insertion into the inguinal duct.
Figure 14:
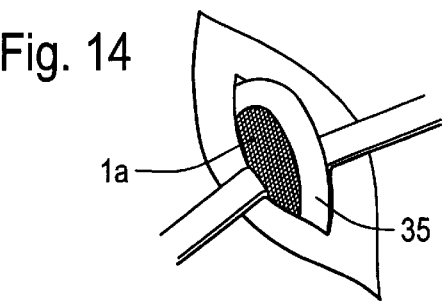
FIG. 14 is a diagrammatic view of the inguinal duct obturated with an obturating implant according to FIGS. 1 and 2.
Figure 15:
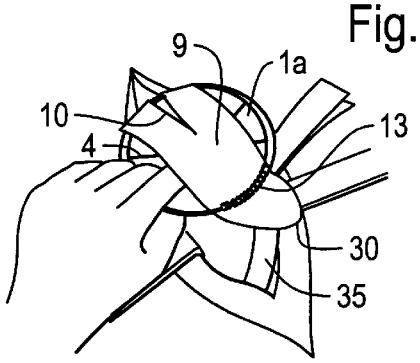
FIG. 15 is a diagrammatic view of the manipulation of an obturating implant according to FIGS. 3 to 5 in order to obturate an inguinal duct, and to protect against recurrences.
Figure 16:
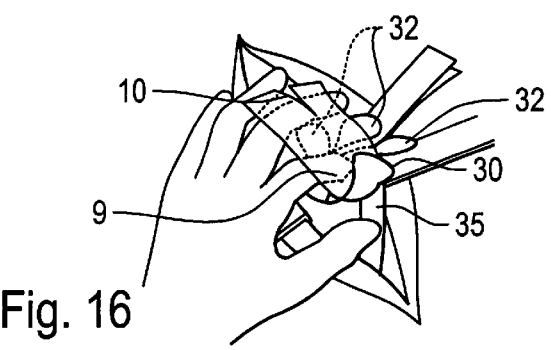
FIG. 16 is a diagrammatic view of the folding of the implant according to FIGS. 3 to 5 and its insertion into the inguinal duct.

At the time of its use, the obturating prosthetic implant 1 is presented facing the duct or the orifice, for example inguinal, as shown diagrammatically in FIGS. 12 to 17. In these figures the reference 35 indicates the spermatic cord. The implant is inserted into the orifice or duct by pressing on the central zone 6 or the geometric center 6a of the panel 2 of the textile element 1a using a finger, forceps or the applicator. In this way the implant changes, by means of a centripetal stress on the remaining periphery of the textile element, which can be applied for example by the walls of the inguinal orifice, from the flat configuration to a configuration gathered up in volume, as illustrated in FIGS. 13, 14 and 16 in particular. In effect, by is compliance, a prosthetic implant according to the invention "molds itself" to the anatomical structures in keeping with the orifice or duct to be obturated, and forms at least two opposite hollow lobes 32, the radial elements 4 guiding the plication and the formation of the lobes, and also conferring on the obturating implant a certain radial strength for better mechanical holding once implanted.

Figure 17:
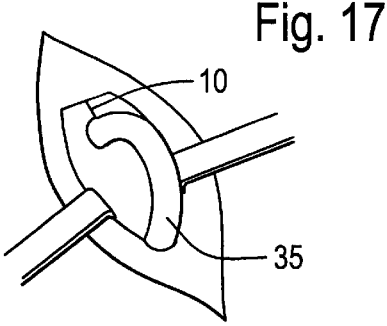
FIG. 17 is a diagrammatic view of the inguinal duct obturated with an obturating implant and an additional covering panel according to FIGS. 3 to 5.

FIGS. 15 to 17 show the application of the implant according to FIGS. 3 to 5, which differs from the above only in that the additional covering panel 9 is positioned above the textile element 1a in such a way as to cover an anatomical zone around the inguinal orifice, in order to prevent possible recurrences, the slit 10 surrounding the spermatic vessels 35, as can be seen in FIG. 17.

Other advantages, specific for hernial surgery, resulting from the obturating prosthetic implant according to the present invention are as follows:

when a third panel of three-dimensional structure is present, in such a way as to be situated on the outside of the implant in its gathered-up configuration, this outer three-dimensional structure is very compliant and soft; it is the only structure in contact with the surrounding tissues, it is not traumatizing in particular for the elements of the spermatic cord and it allows very good rehabilitation;

the radial elements, providing the mechanical holding of the obturating prosthetic implant, are not in contact with critical elements such as the vas deferens, the spermatic, iliac or femoral vessels or the regional nerves;

the stopping of the radial elements at the level of the central zone allows the deep end of the prosthetic implant, in its gathered-up configuration, once in position, not to be traumatizing or perforating with respect to the peritoneal structures and to adapt to the thickness of the abdominal wall;

in the embodiment with a third panel of three-dimensional structure, all of the potentially fragile zones are protected from recurrences (direct orifice in the case of indirect hernia treatment and vice-versa) using one and the same implant;

in the embodiment with an additional covering panel, integral with the textile element, the fixing of the latter to the peripheral tissues contributes to preventing the risks of deep migration in the prosthetic implant;

the very high porosity of the textile element allows deep conjunctive rehabilitation, bridging the space and thus filling the orifice in a stable manner;

in the embodiment with a third panel of three-dimensional structure, the overstitching advantageously makes it possible not to crush the upper panel on the lower panels as would have been done by conventional sewing, and thus to preserve the compliant three-dimensional structure over the whole of the useful outer surface of the implant.

What is claimed is:

1. A prosthetic implant for obturating an anatomical duct, cavity or orifice, comprising: a porous textile element obtained from a prosthetic fabric, having a flat and nongathered up configuration in the shape of a patch with a continuous outer edge, said textile element comprising a central zone and a peripheral zone, said peripheral zone comprising at least two superposed panels of prosthetic fabric and at least two radial elements of textile strip shape consisting of a multiplicity of stitches linking said two panels with at least one thread, said central zone being free from said radial elements, wherein said radial elements determine, by local thrust in said central zone while centripetally stressing the remaining periphery of said textile element, a configuration gathered up in volume.

2. The implant as claimed in claim 1, wherein, in the gathered-up configuration, said two radial elements determine at least two opposite lobes formed by said two panels between said radial elements.

3. The implant as claimed in claim 1, wherein said radial elements each extend radially from the outer edge of said textile element to an intermediate point between a geometric center of said textile element and the outer edge of said textile element.

4. The implant as claimed in claim 1, wherein said radial elements each extend radially up to said central zone.

5. The implant as claimed in claim 3, wherein said radial elements each extend radially over a limited length, starting from and in the vicinity of the outer edge.

6. The implant as claimed in claim 1, wherein said two panels are connected to each other by discontinuous overstitching along the outer edges of said panels.

7. The implant as claimed in claim 1, wherein said radial elements tie said panels.

8. The implant as claimed in claim 1, wherein said textile element comprises at least three panels bound to each other.

9. The implant as claimed in claim 8, wherein said textile element is capable of being obtained by cutting out a circular patch bringing together an outer panel, an intermediate panel and an inner panel, by folding said patch along a diameter (d) with two sides facing each other and radial elements connecting the three panels together and at least two elements connecting two facing sides of said inner panel.

10. The implant as claimed in claim 8, wherein said radial elements connect two panels to each other, said third panel being connected to said other two panels by overstitching its outer edge.

11. The implant as claimed in claim 1, comprising an additional covering panel, bound to said textile element, having a shape different from that of said textile element and adapted with an appropriate slit for surrounding any anatomical duct.

12. An assembly for obturating an anatomical duct, cavity or orifice, comprising an obturating implant as claimed in claim 1, and an applicator.

* * * * *